United States Patent [19]

Halskov

[11] Patent Number: 4,664,256
[45] Date of Patent: May 12, 1987

[54] PACKAGED STABLE ENEMA SOLUTION OR SUSPENSION CONTAINING 5-AMINOSALICYCLIC ACID

[75] Inventor: Søren Halskov, Helsinge, Denmark

[73] Assignee: Farmaceutisk Laboratorium Ferring A/S, Vanlose, Denmark

[21] Appl. No.: 782,159

[22] Filed: Oct. 2, 1985

Related U.S. Application Data

[63] Continuation of Ser. No. 529,769, Sep. 6, 1983, abandoned.

[51] Int. Cl.$^4$ .................... B65D 81/24; A61K 31/60
[52] U.S. Cl. ................................. 206/213.1; 514/166
[58] Field of Search .................... 206/204, 205, 213.1; 264/55, 102; 514/166, 159

[56] References Cited

U.S. PATENT DOCUMENTS

| | | | |
|---|---|---|---|
| 3,044,118 | 7/1962 | Bernhardt et al. | 264/85 |
| 3,621,892 | 11/1971 | Gillespie | 264/102 |
| 3,937,778 | 2/1976 | Tanaka | 264/85 |
| 4,150,744 | 4/1979 | Fennimore | 206/205 |
| 4,340,550 | 7/1982 | Ho | 264/85 |
| 4,447,373 | 5/1984 | Chappell et al. | 264/102 |

FOREIGN PATENT DOCUMENTS

| | | |
|---|---|---|
| 2712934 | 4/1977 | Fed. Rep. of Germany . |
| WO81/02671 | 1/1981 | Int'l Pat. Institute . |
| WO81/02672 | 6/1981 | Int'l Pat. Institute . |

OTHER PUBLICATIONS

Khan et al, "An Experiment to Determine the Active Therapeutic Moiety of Sulphasalazine", Lancet, Oct. 29, 1977, pp. 892-895.
Campieri et al, "Treatment of Ulcerative Colitis with High-Dose 5-Amino-Salicyclic Acid Enemas", Lancet, Aug. 8, 1981, pp. 270-271.
Allgayer et al, "Determination of the PK Values of 5-Aminosalicyclic Acid and N-acetylaminosalicyclic Acid and Comparison of the pH Dependent Lipid-Water Partition Coefficients of Sulphasalizine and its Metabolites", Arzneim, Forsch. 35(II), No. 9 (1985), p. 1457-5.
Rhodes, "Medical Treatment of Ulcerative Colitis and Crohn's Disease", Journal of Clinical and Hospital Pharmacy (1983), 8, 219-232.
Bondesen, S. et al, "5-Aminosalicylic Acid Enemas in Patients with Active Ulcertative Colitis", Scand. J. Gastroenterol 19: 677-687 (1984).
Binder, V., "Tropical 5-Aminosalicyclic Acid Versus Prednisolone in Ulcerative Proctosigmoiditis", Digestive Diseases and Sciences, U.S.A., Oct. 3, 1985.
Willoughby, C. et al, "5-Aminosalicyclic Acid (PENTASA) in Enema Form for the Treatment of Active Ulcerative Colitis", Submitted to Scand. J. Gastroenterol.

Primary Examiner—William Price
Assistant Examiner—Jimmy G. Foster
Attorney, Agent, or Firm—Fleit, Jacobson, Cohn & Price

[57] ABSTRACT

A packaged enema solution or suspension consisting essentially of an effective amount of 5-ASA or a pharmaceutically acceptable salt or ester thereof, a chelating agent, an antioxidant and a buffer, the solution or suspension having a pH value of from 4 to 7 and being contained in a plastic bottle under an inert gas, the plastic bottle being packaged in a diffusion-tight light-impervious package in the same inert gas as is present in the bottle.

13 Claims, 1 Drawing Figure

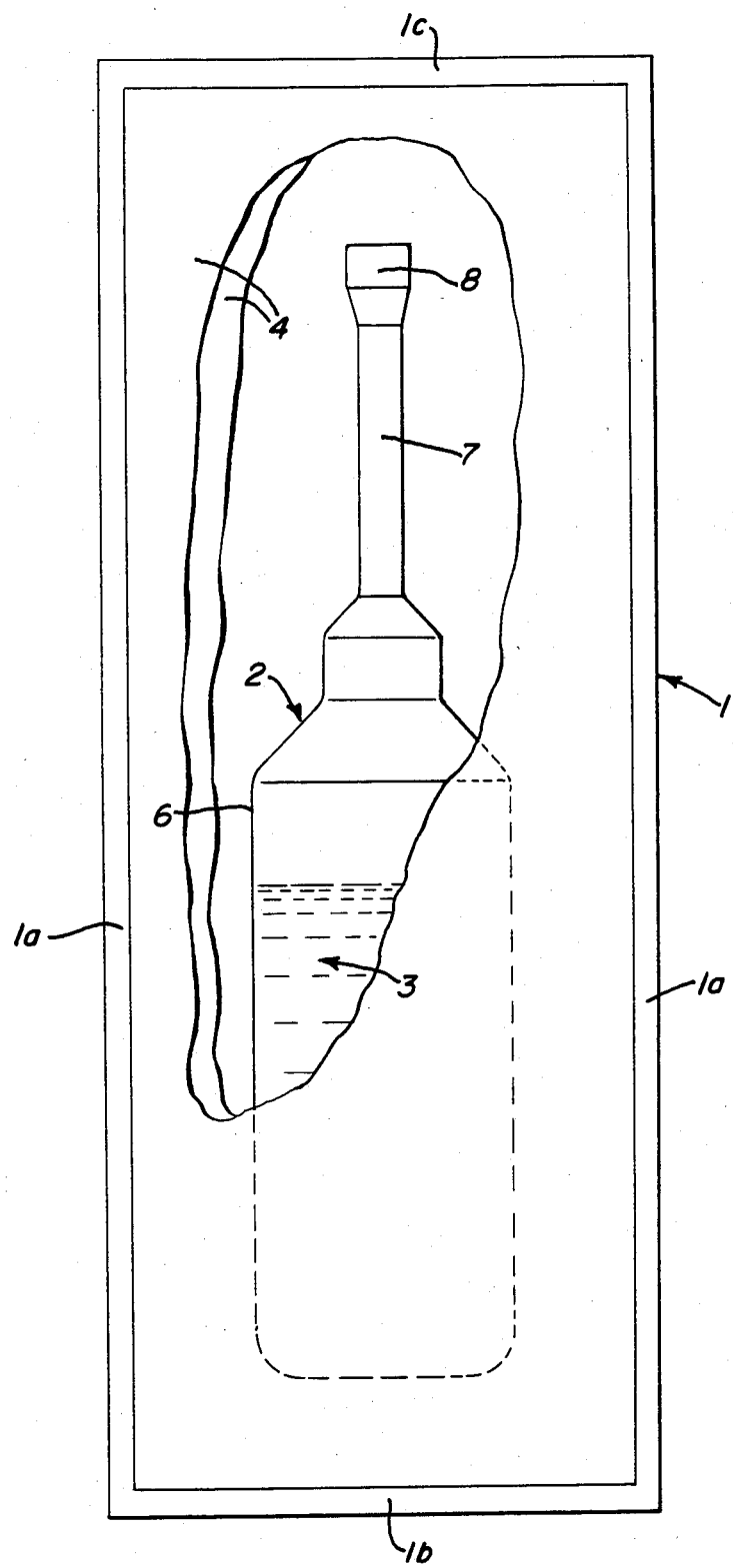

4,664,256

PACKAGED STABLE ENEMA SOLUTION OR SUSPENSION CONTAINING 5-AMINOSALICYCLIC ACID

This application is a continuation of application Ser. No. 529,769, filed Sept. 6, 1983, now abandoned.

BACKGROUND OF THE INVENTION

1. Field of the Invention

This invention concerns an enema solution or suspension which is suitable for rectal administration of 5-aminosalicyclic acid (5-ASA) in mammals. The present enema solutions are useful in the treatment of bowel diseases, in particular, ulcerative colitis, Crohn's disease located in the colon and proctoigmoiditis.

2. Statement of the Prior Art

Salicyclazosulfapyridine (SASP) has for a long period of time been a cornerstone in the treatment of ulcerative colitis and has been used in various pharmaceutical dosage forms including enemas. When SASP reaches the colon, it is split by bacteria into sulfapyridine (SP) and 5-ASA and, as explained in detail in copending U.S. application Ser. No. 555,533, filed Nov. 28, 1983, which is a continuation application of Ser. No. 270,517, filed May 29, 1981, now abandoned, and based on International Application No. WO 81/02671, both of which are incorporated by reference, most experts now hold the active moiety of SASP to be 5-ASA.

Azad Khan et al, Lancet, 1977, pp. 892–95, compared suspensions of SASP, SP and 5-ASA administered rectally and concluded that the therapeutic active moiety was 5-ASA and that SP only acts as a carrier to ensure that 5-ASA is not released until it has reached the colon. Stability tests showed that SASP and SP suspensions were stable at room temperature while the 5-ASA suspension showed some decay and had to be made up in fresh batches every three months and stored in a refrigerator until used.

Similar observations were made by Cámpieri et al, Lancet, Aug. 8, 1981, pp. 220–21, who carried out a comparison trial between 5-ASA and hydrocortisone. Since 5-ASA turned brown in solution, they added charcoal to the hydrocortisone as coloring agent in order to ensure double-blindness.

While enemas containing 5-ASA have thus proved useful in the treatment of ulcerative colitis, their limited stability is a major problem and a solution to this problem would be of great advantage.

It has now been discovered that the desired stability can be obtained by packaging an aqueous solution or suspension of 5-ASA or a pharmaceutically acceptable salt or ester thereof being contained in a plastic bottle under an inert gas in a diffusion-tight package impervious to light in the same inert gas as was used in the plastic bottle.

The 5-ASA solution or suspension should further contain a chelating agent, an antioxidant and a buffer in order to provide a pH value of from 4 to 7.

The presence of the same inert gas on both sides of the plastic bottle provides an equilibrium which effectively cooperates with the various stabilizers and the diffusion-tight light- impervious package and provides a stability of a year or more.

SUMMARY OF THE INVENTION

Hence, the invention concerns a packaged enema solution or suspension consisting essentially of an effective amount of 5-ASA or a pharmaceutically acceptable salt or ester thereof, a chelating agent, an antioxidant and a buffer, said solution or suspension having a pH value of from 4 to 7 and being contained in a plastic bottle under an inert gas, said plastic bottle being packaged in a diffusion-tight light-impervious package in the same inert gas as is present in the bottle.

BRIEF DESCRIPTION OF THE DRAWING

The invention will be further illustrated with reference to the accompanying single figure of drawing which shows a partly torn away package containing a liquid-filled enema bottle.

The drawing shows a laminated foil package 1 enclosing an anema bottle 2 containing an enema solution or suspension 3.

The laminated foil package 1 is heat-sealed along each edge at 1a and along the bottom at 1b and the top at 1c, respectively.

Preferably, the package is formed from a heat-sealable plastic-metal laminate, e.g., a polyethylene-aluminum laminate 4.

The bottle is constituted by a container part 6, an intermediate part 7 and a sealed closure part 8.

DETAILED DESCRIPTION OF THE INVENTION

The therapeutically active ingredient 5-ASA may be present in the form of the free acid or a pharmaceutically acceptable salt or ester thereof.

The salts of 5-ASA may be acid addition salts, in particular, the hydrochloride, but any pharmaceutically acceptable, non-toxic organic or inorganic acid may be used.

Also, salts formed with the carboxylic acid group may be used. As examples may be mentioned alkali metal salts (K, Na), alkaline earth metal salts (Ca, Mg), but again any pharmaceutically acceptable, non-toxic salt may be used. The Na- and Ca- salts are preferred.

In German Offenlegungsschrift No. 2,712,934, a number of esters of ortho-, meta- and para-salicyclic acid are disclosed. Said esters are effective as ultraviolet ray screening compounds thereby rendering themselves useful in preventing solar burning. The disclosed meta- (or 5-) aminosalicyclic esters and a number of related esters are also applicable in the enema according to the invention.

Applicable esters are, e.g., straight chain or branched $C_1$–$C_{18}$ alkyl esters such as methyl, ethyl, propyl, isopropyl, butyl, isobutyl, amyl, hexyl, heptyl, octyl, nonyl, decyl, lauryl, myristyl, cetyl, and stearyl, etc.; straight chain or branched $C_2$–$C_{18}$ alkenyl esters, e.g., vinyl, allyl, undecenyl, oleyl, linolenyl, etc.; $C_3$–$C_8$ cycloalkyl esters, e.g., cyclopropyl, cyclobutyl, cyclopentyl, cyclohexyl, cycloheptyl and cyclooctyl, etc.; aryl esters, e.g., phenyl, toluyl, xylyl, naphthyl, etc.; alicyclic esters, e.g., menthyl, etc.; or aralkyl esters, e.g., benzyl, phenethyl, etc.

Generaly speaking, the proper selection of the active ingredient depends on the selected type of formulation, the disease pattern, especially the site and type of the disease, and the desired release of the active ingredient, as shall be further expounded below together with the concept "effective amount".

The physical state and solubility characteristics of the 5-ASA derivatives must be taken into account when selecting a suitable carrier composition for the ingredient.

The preferred active ingredient at present is the free acid, 5-ASA.

Preferably, the 5-ASA is extremely pure in order to prevent autooxidation. The purity is manifested by the absence of additional high pressure liquid chromatography (HPLC) peaks (both determined fluospectrophotometrically and spectrophotometrically in general).

The effective amount of the 5-ASA or ester or salt thereof contained in the enema depends upon the extent of the disease and for adults generally in amounts of from 0.2 to 4 g 5-ASA per 100 ml enema will be used. Whether or not the enema- is a suspension or solution i.a. depends on the amount of 5-ASA and the pH. The solubility of 5-ASA in water is about 2 g/100 ml at pH 7, but only about 0.2 g/100 ml at pH 4.8.

By administering an enema suspension, which might be provided at the more acidic pH values in the range from 4 to 7, a kind of slow-release of the 5-ASA might be obtained.

Since 5-ASA is assumed to be topically effective at the ulcer sites in case of colitis such slow release is believed to be the most beneficial to the patient.

The enema solution or suspension also contains a chelating agent to avoid autooxidation catalyzed by metal ions which may be present even in analytic grade chemicals. Any of the classic chelating agents may be used, but the preferred chelating agents are polymethylene diaminetetraacetic acid, in particular, ethylene diaminetetraacetic acid (EDTA) and its alkali metal salts. The preferred amount of chelating agent is from 5 to 30 mg/100 ml solution or suspension, preferably about 20 mg/100 ml.

Further, the solution or suspension contains an antioxidant to prevent oxidation of the 5-ASA. Preferred antioxidants are sodium or potassium pyrosulfite, but other well-known antioxidants might be used, e.g., ascorbic acid. The preferred amount is 50–200 mg/100 ml suspension or solution, preferably about 100 mg/100 ml.

Further, the enema solution contains a suitable buffer in order to maintain the desired pH value in the range of from 4 to 7. The preferred pH is from 4.5 to 5, in particular, about 4.8. This pH is advantageously established by means of a citric acid buffer since citric, acid has a pka of 4.77.

Other applicable buffers are bicarbonate buffers if a pH of 6 to 7 is desired since the pka for bicarbonate is 6.5.

Generally speaking, any buffer system might be used which provides the proper pH and does not interfere with the other components of enema.

The gas used in the bottle and the package should be inert with relation to the solution or suspension. Preferred inert gases are nitrogen or argon, but also carbon dioxide may be used if the solution or suspension contains a bicarbonate buffer.

The plastic bottle is preferably made by blow forming from a polyethylene granulate which has been deoxidized by alternating vacuum and nitrogen treatments.

The diffusion-tight light-impervious package material is preferably made from a heat-sealable plastic-metal laminate, e.g., plastic-aluminum laminate, where any heat-sealable plastic material, e.g., polyethylene, might be used.

DESCRIPTION OF THE PREFERRED EMBODIMENT

A packaged suspension according to the invention may be prepared as follows:

1. Preparation of a 5-ASA suspension

| | |
|---|---|
| 5-ASA* | 1 g/100 ml |
| EDTA | 20 mg |
| Sodium pyrosulfite | 0.2 g |
| Citric acid | 1 g |
| Sodium hydroxide | q.s. (up to pH = 4.8 about 0.35 g) |
| Sterile water | up to 100 ml |

*5-ASA is extremely pure to avoid autooxidiation - no additional HPLC peaks (both fluospectrophotometrically and spectrophometrically in general).

The suspension is prepared and dispensed in an inert gas, e.g., nitrogen or argon.

2. Filling of 5-ASA suspension in a plastic bottle

The polyethylene granulate is deoxidized by alternating vacuum and nitrogen treatments. The deoxidized granulate is extruded, formed by blowing and the 5-ASA suspension is filled into a plastic bottle blower/packing machine. The inert gas used for dispensing also constitutes the supporting air, blowing air and the air in the chamber in which the filling and forming procedures are taking place.

The bottle is conveyed directly to a packing chamber containing the same inert gas in which the bottles are packed in aroma-tight, light-impervious (plastics aluminum laminate) bags which are sealed by welding before they drop into the atmosphere.

Enema suspensions contain 1 g and 2 g 5-ASA per 100 ml prepared in analogy with the above procedure have been tested for stability by fluospectrophotometry and HPLC.

After storage at room temperature for more than a year, no signficant change was observed neither with regard to color or 5-ASA content.

It is also to be understood that the following claims are intended to cover all of the generic and specific features of the invention herein described, and all statements of the scope of the invention which, as a matter of language, might be said to fall therebetween.

What is claimed is:

1. A packaged enema solution or suspension consisting essentially of an effective amount of 5-ASA or a pharmaceutically acceptable salt or ester thereof, a chelating agent, an antioxidant and a buffer, said solution or suspension having a pH value of about 4.8 and being contained in a plastic bottle under an inert gas, said plastic bottle being packaged in a diffusion-tight light-impervious package in the same inert gas as is present in the bottle.

2. A packaged enema solution or suspension according to claim 1, wherein the chelating agent comprises EDTA, the antioxidant comprises sodium pyrosulfite and the buffer comprises citric acid and sodium hydroxide.

3. A packaged enema solution or suspension according to claim 1, wherein the buffer is sodium bicarbonate and hydrochloric acid.

4. An enema solution or suspension according to claim 1, wherein the 5-aminosalicyclic acid is sufficiently pure to avoid autooxidation, having no additional HPLC fluospectrophotometric and spectrophotometric peaks.

5. A packaged enema solution or suspension according to claim 1, wherein the inert gas is argon, nitrogen or carbon dioxide.

6. A packaged enema solution or suspension according to claim 1 consisting essentially of substantially pure 5-aminosalicyclic acid or a pharmaceutically acceptable salt or ester thereof, ethylenediaminetetraacetic acid, sodium pyrosulfite, citric acid, sodium hydroxide and purified water.

7. A packaged enema solution or suspension according to claim 1, wherein the plastic bottle is polyethylene.

8. A packaged enema solution or suspension according to claim 7, wherein a polyethylene granulate used for producing the polyethylene bottle is deoxidized by alternately evacuating the granulate and flooding the granulate with nitrogen gas.

9. A package enema solution or suspension according to claim 8, wherein the deoxidized granulate is extruded, formed into a bottle by means of an inert gas, and the bottle is filled with said enema solution.

10. A package enema solution or suspension according to claim 9, the filled bottle is conveyed directly to a packing chamber wherein the bottle is packed into an aroma-tight bag under an inert gas, said bag being sealed by welding before being contacted with air.

11. A packaged enema solution or suspension according to claim 10, wherein the aroma-tight bag is a plastic aluminum laminate.

12. A packaged enema solution or suspension according to claim 11, containing per 100 ml of solution about 0.2 to 4.0 g 5-aminosalicyclic acid, about 50 mg to 200 mg of sodium pyrosulfite, about 0.5 to 1.5 g citric acid, about 0.5 to 2 g sodium hydroxide, about 5 to 30 mg sodium EDTA, and purified water.

13. A packaged enema solution or suspension according to claim 12, containing per 100 ml of solution about 1 g of 5-aminosalicyclic acid, about 200 mg of sodium pyrosulfite, about 1 g citric acid, about 20 mg sodium EDTA, and sufficient sodium hydroxide and purified water to maintain said pH of 4.8.

* * * * *